United States Patent [19]

Nusslein et al.

[11] 4,183,739
[45] Jan. 15, 1980

[54] 2-(DIMETHYLCARBAMOYLIMINO)-BENZ-THIAZOLINE-3-CARBOXYLIC ACID ESTERS, AND HERBICIDAL COMPOSITIONS CONTAINING SAME

[75] Inventors: Ludwig Nüsslein; Friedrich Arndt, both of Berlin, Fed. Rep. of Germany

[73] Assignee: Schering AG, Berlin and Bergkamen, Fed. Rep. of Germany

[21] Appl. No.: 835,530

[22] Filed: Sep. 22, 1977

[30] Foreign Application Priority Data

Sep. 30, 1976 [DE] Fed. Rep. of Germany ....... 2644425

[51] Int. Cl.$^2$ .............................................. C07D 277/82
[52] U.S. Cl. ............................................ 71/90; 548/163
[58] Field of Search ............................. 260/305; 71/90

[56] References Cited

U.S. PATENT DOCUMENTS

| | | | |
|---|---|---|---|
| 2,851,391 | 9/1958 | Gerjovich et al. | 260/305 |
| 3,501,285 | 3/1970 | Baldwin | 260/304 D |
| 3,654,296 | 4/1972 | Bohhofer | 260/304 D |
| 3,828,001 | 8/1974 | Broad et al. | 71/90 |
| 3,967,950 | 7/1976 | Kano et al. | 260/305 |
| 3,989,505 | 11/1976 | Nickell | 71/90 |
| 4,013,681 | 3/1977 | Karabinos et al. | 71/90 |

*Primary Examiner*—Nicholas S. Rizzo
*Attorney, Agent, or Firm*—Michael J. Striker

[57] ABSTRACT

2-(Dimethylcarbamoylimino)-benzthiazoline-3-carboxylic acid ester of the formula

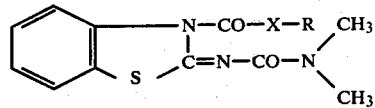

in which R is an aliphatic hydrocarbon, a substituted aliphatic hydrocarbon, an aromatic hydrocarbon or a substituted aromatic hydrocarbon and X is oxygen or sulfur.

The compounds have an excellent selectivity action in regard to agricultural plants and also possess a superior herbicidal activity against mono- and di-cotyl weeds.

14 Claims, No Drawings

2-(DIMETHYLCARBAMOYLIMINO)-BENZ-THIAZOLINE-3-CARBOXYLIC ACID ESTERS, AND HERBICIDAL COMPOSITIONS CONTAINING SAME

BACKGROUND OF THE INVENTION

The invention relates to 2-(dimethylcarbamoylimino)-benzthiazoline-3-carboxylic acid esters.

(Benzthiazol-2-yl)-urea derivatives with herbicidal activity have already become known, see U.S. Pat. No. 2,756,135. These agents, however, have only a limited selective-herbicidal action.

It is therefore an object of the present invention to provide for an agent which has a superior selective-herbicidal action.

SUMMARY OF THE INVENTION

This object is met by a compound which is a 2-(dimethylcarbamoylimino)-benzthiazoline-3-carboxylic acid ester of the formula

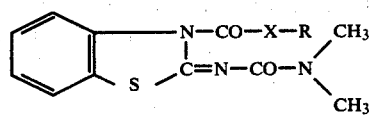

in which R is an aliphatic hydrocarbon, a substituted aliphatic hydrocarbon, an aromatic hydrocarbon or a substituted aromatic hydrocarbon and X is oxygen or sulfur. The compounds of the invention are characterized by a superior selectivity towards agricultural plants and in addition have an excellent herbicidal action against mono- and di-cotyl weeds.

Their selectivity is particularly remarkable in regard to such agricultural plants as, for instance, sugar beets, peanuts, potatoes, peas, maize, rice, seed sorghum and various types of grains.

The compounds are particularly suited to suppress weeds and weed-type grasses of the genera Stellaria, Senecio, Matricaria, Lamium, Centaurea, Amaranthus, Chrysanthemum, Ipomea, Polygonum, Alopecurus, Digitaria, Poa, and others.

DETAILS OF THE INVENTION AND PREFERRED EMBODIMENTS

The compounds of the invention are preferably used in amounts of about 1 to 5 kg of active agent per 2.5 acres (1 hectare).

The compounds of the invention may be used either by themselves or intermixed with each other or in mixture with other active agents.

Depending on the particular purpose of use the following herbicidal agents may be employed together with the compounds of the invention. These other agents may be admixed, if desired, immediately prior to use of the inventive compounds.

substituted anilines,
substituted aryloxycarboxylic acids and their salts, esters and amides,
substituted ethers,
substituted arsonic acids and their salts, esters and amides,
substituted benzimidazoles,
substituted benzisothiazoles,
substituted benzthiadiazinone dioxides,
substituted benzoxazines,
substituted benzoxazinones,
substituted benzthiazoles,
substituted benzthiazoles,
substituted biurets,
substituted quinolines,
substituted carbamates,
substituted aliphatic carboxylic acids and their salts, esters and amides,
substituted aromatic carboxylic acids and their salts, esters and amides,
substituted carbamoylalkyl-thio- or dithiophosphates
substituted quinazolines,
substituted cycloalkylamidocarbonylthiol acids and their salts, esters and amides,
substituted cycloalkylcarbonylamido-thiazoles,
substituted dicarboxylic acids and their salts, esters and amides,
substituted dihydrobenzofuranylsulfonates,
substituted disulfides,
substituted dipyridyl salts,
substituted dithiocarbamates,
substituted dithiophosphoric acids and their salts, esters and amides,
substituted urea derivatives,
substituted hexahydro-1H-carbothioates,
substituted hydantoines,
substituted hydrazides,
substituted hydrazonium salts,
substituted isoxazolpyrimidones,
substituted imidazoles,
substituted isothiazolpyrimidones,
substituted ketones,
substituted naphthoquinones,
substituted aliphatic nitriles,
substituted aromatic nitriles,
substituted oxadiazoles,
substituted oxadiazinones,
substituted oxadiazolidinediones,
substituted oxadiazinediones,
substituted phenols and their salts and esters,
substituted phosphonic acids and their salts, esters and amides,
substituted phosphoniumchlorides,
substituted phosphonalkylglycines,
substituted phosphites,
substituted phosphoric acids and their salts, esters and amides,
substituted piperidines,
substituted pyrazoles,
substituted pyrazolalkylcarboxylic acids and their salts, esters, and amides,
substituted pyrazolium salts,
substituted pyrazoliumalkylsulfates,
substituted pyridazines,
substituted pyridazones,
substituted pyridine-carboxylic acids and their salts, esters and amides,
substituted pyridines,
substituted pyridinecarboxylates,
substituted pyridinones,
substituted pyrimidones,
substituted pyrrolidine-carboxylic acids and their salts, esters and amides,
substituted pyrrolidines,
substituted arylsulfonic acids and their salts, esters and amides,
substituted styrenes, substituted tetrahydro-oxadiazindiones,
substituted tetrahydromethanoindenes,
substituted tetrahydro-diazol-thiones,
substituted tetrahydro-thiadiazine-thiones,
substituted tetrahydro-thiadiazinediones,
substituted thiadiazoles,
substituted aromatic thiocarboxylic acid amides,
substituted thiocarboxylic acids and their salts, esters and amides,
substituted thiolcarbamates,
substituted thiophosphoric acids and their salts, esters and amides,
substituted triazines,
substituted triazoles
substituted uracils, and
substituted urethidindiones.

It is possible to use also other additives, for instance, non-phytotoxic additives which, in case of herbicides result in a synergistic increase of activity, such as, wetting agents, emulsifying agents, solvents and oily additives.

The compounds of the invention or their mixtures are suitably employed in the form of compositions such as powders, dusting agents, granulates, solvents, emulsions, or suspensions. In the composition there may be used a liquid and/or solid carrier material or diluent and, if desired, a wetting agent adhesion promoting agent, emulsifier, and/or dispersion agent.

Suitable liquid carrier materials are, for instance, water, aliphatic and aromatic hydrocarbons, such as, benzene, toluene, xylene, cyclohexanone, isophorone, dimethylsulfoxide, dimethylformamide, and furthermore mineral oil fractions.

As solid carrier materials there may be used mineral earths, for instance, tonsil, silicagel, talc, kaolin, attaclay, limestone, silicic acid and plant products, for instance flours.

There may also be added surface active agents, for instance, calciumlignosulfonate, polyoxyethylenealkylphenyl-ethers, naphthalinesulfonic acids and their salts, phenolsulfonic acid and their salts, formaldehyde condensation products, fatty alcoholsulfates, as well as substituted benzosulfonic acids and their salts.

The proportion of the active agent or agents in the total composition can be varied widely. The compositions for instance may be about 10 to 80% by weight of active agents, about 90 to 20% by weight of liquid or solid carrier materials and, if desired, up to 20% by weight of surface active agents.

The application of the composition can be effected in conventional form, for instance by using water as the carrier material in a spray composition containing about 100 to 1000 liter of composition per about 2.5 acres. The application of the compositions is possible in the so-called "low-volume" and "ultra-low-volume process" as well as in the form of so-called micro granulates.

Among the compounds of the invention those have a particularly outstanding selective-herbicidal action wherein in the above-given formula R is alkyl of 1 to 8 carbon atoms, alkenyl of 2 to 8 carbon atoms, alkinyl of 2 to 8 carbon atoms, phenyl, a phenyl radical which is substituted by one, two, or three halogen atoms and/or alkyl of 1 to 3 carbon atoms and/or alkoxy of 1 to 3 carbon atoms and/or alkamino of 1 to 3 carbon atoms and/or trihalogeno methyl, a phenyl-alkyl residue wherein alkyl has 1 to 2 carbon atoms or a mono- or di-halogeno benzyl residue, X always being oxygen or sulfur.

Preferred among these compounds are those wherein R is methyl, ethyl, propyl, isopropyl, 2-propenyl, 2-propinyl, butyl, isobutyl, tert.-butyl, sec. butyl, pentyl, isopentyl, hexyl, heptyl, octyl, phenyl, chlorophenyl, dichlorophenyl, benzyl, chlorobenzyl, dichlorobenzyl, X again being oxygen or sulfur.

PROCESS OF MAKING

The compounds which have not been described so far in the literature may be made by for instance the following processes:

I. A metal compound of the formula

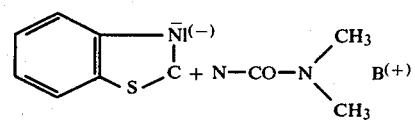

in which $B^{(+)}$ is a univalent metal equivalent, preferably a lithium, sodium, or potassium atom, is reacted with a halogenoformic acid ester of the formula Hal—CO—X—R in which Hal stands for halogen, and X and R have the same meaning as in the above broad formula.

II. 1-(benzthiazol-2-yl)-3,3-dimethyl-urea of the formula

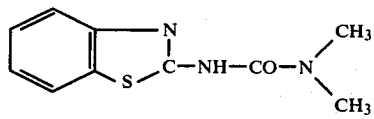

is reacted in the presence of an acid acceptor with a halogenoformic acid ester of the formula Hal—CO—X—R in which Hal, X and R have the same meaning as given above in the process identified as I, or in the above general formula.

The reaction may be carried out in both cases at a temperature between 0° and 120° C., preferably at room temperature. The components are preferably used in about equimolar amounts.

As reaction medium there are used polar organic solvents. Their selection by established principles depends on the type of metal compound, on the halogenoformic acid ester and the employed acid acceptor. As solvents or suspension agents there may for instance be used acid amides, such as dimethylformamide, acid nitriles like acetonitrile; ethers like dioxane; ketones like acetone, and many others.

As acid acceptors there can be used the conventional agents employed for this purpose. Suitable are for instance organic bases, such as tertiary amines, for instance triethylamine or N,N-dimethylaniline, pyridine bases or also inorganic bases, like oxides, hydroxides, and carbonates of the alkali and alkali earth metals. Bases used in liquid form such as pyridine can at the same time serve as solvents.

The isolation of the formed compounds of the invention is effected at the end of the reaction by distilling off the solvent or by precipitation with water.

The starting materials used in the above processes are known compounds.

The following examples will further illustrate the invention.

EXAMPLE 1

20.44 g of 2-(dimethylcarbamoylimino)-benzothiazoline-3-id, lithium salt were suspended in 250 ml of acetonitrile and were reacted under stirring and dropwise with 11.3 g of chloroformic acid isopropylester at room temperature. To complete the reaction stirring was continued for 30 minutes. The reaction mass was then poured into 1.5 l of icewater, whereupon the formed precipitate was removed by suction and subjected to recrystallization from isopropyl ether.

Yield: 17.1 g (61.9 of the theoretical value of 2-(dimethylcarbamoylimino)-benzthiazoline-3-carboxylic acid isopropylester; m.p. 105° C.

Analysis: Calculated: C, 54.70%; H, 5.58%; N, 13.67%. Obtained: C, 55.11%; H, 5.98%; N, 13.94%.

EXAMPLE 2

A solution of 30.13 g of 1-(benzothiazol-2-yl)-3,3-dimethyl urea in 250 ml of pyridine were added upon stirring at room temperature dropwise to 16.95 g of chlorothioformic acid-S-ethylester.

The solution was then subjected to further stirring for 30 minutes and was added to six times its amount of icewater. After distilling off the solvent the precipitated compound was recrystallized from isopropyl ether. There were obtained 26.35 g (62.5% of the theoretical value) of 2-(dimethylcarbamoylimino)-benzothiazoline-3-thiocarboxylic acid-S-ethylester; m.p. 138° C.

Analysis: Calculated: C, 50.46%; H, 4.89%; N, 13.58%. Obtained: C, 51.03%; H, 5.01%; N, 13.68%.

In an analogous manner the following compounds of the invention were made:

| Compound | Physical constants | |
|---|---|---|
| 2-(dimethylcarbamoylimino)-benzothiazoline-3-carboxylic acid methylester | m.p. | 134° C. |
| 2-(dimethylcarbamoylimino)-benzothiazoline-3-carboxylic acid butylester | m.p. | 80° C. |
| 2-(dimethylcarbamoylimino)-benzothiazoline-3-carboxylic acid-(2-propenyl)-ester | m.p. | 102° C. |
| 2-(dimethylcarbamoylimino)-benzothiazoline-3-carboxylic acid pentylester | m.p. | 69° C. |
| 2-(dimethylcarbamoylimino)-benzothiazoline-3-carboxylic acid isobutylester | m.p. | 89° C. |
| 2-(dimethylcarbamoylimino)-benzothiazoline-3-carboxylic acid-(2-propinyl)-ester | m.p. | 136° C. |
| 2-(dimethylcarbamoylimino)-benzothiazoline-3-carboxylic acid benzylester | m.p. | 137° C. |
| 2-(dimethylcarbamoylimino)-benzothiazoline-3-carboxylic acid phenylester | m.p. | 148° C. |

The compounds of the invention are colorless, non-smelling crystalline bodies which are insoluble in water and hydrocarbons, but have a moderate to good solubility in other organic solvents like halogenated hydrocarbons, ethers, ketones, alcohols, carboxylic acids, esters, carboxylic acid amides, carboxylic acid nitriles, and many others.

The application and activity of the compounds is illustrated by the following examples:

EXAMPLE 3

The compounds listed below in Table 1 were applied by spraying in amounts of 5 kg of active agent per about 2.5 acres suspended in 600 liters of water per about 2.5 acres to Sinapis and Solanum. The application was made in a hot house in tests involving preemergence and in tests involving postemergence application. 3 weeks after application the results were evaluated on a scale from 0=no effect, to 4=total destruction of the plants.

As appears from the table, normally a total destruction of the test plants was accomplished.

TABLE I

| Compounds | Preemergence application | | Postemergence application | |
|---|---|---|---|---|
| | Sinapis | Solanum | Sinapis | Solanum |
| 2-(dimethylcarbamoylimino)-benzothiazoline-3-carboxylic acid methylester | 4 | 4 | 4 | 4 |
| 2-(dimethylcarbamoylimino)-benzothiazoline-3-carboxylic acid butylester | 4 | 4 | 4 | 4 |
| 2-(dimethylcarbamoylimino)-benzothiazoline-3-carboxylic acid-(2-propenyl)-ester | 4 | 4 | 4 | 4 |
| 2-(dimethylcarbamoylimino)-benzothiazoline-3-carboxylic acid pentylester | 4 | 4 | 4 | 4 |
| 2-(dimethylcarbamoylimino)-benzothiazoline-3-carboxylic acid isobutylester | 4 | 4 | 4 | 4 |
| 2-(dimethylcarbamoylimino)-benzothiazoline-3-carboxylic acid isopropylester | 4 | 4 | 4 | 4 |
| 2-(dimethylcarbamoylimino)-benzothiazoline-3-carboxylic acid-(2-propinyl)-ester | 4 | 4 | 4 | 4 |
| 2-(dimethylcarbamoylimino)-benzothiazoline-3-carboxylic acid benzylester | 4 | 4 | 4 | 4 |
| 2-(dimethylcarbamoylimino)-benzothiazoline-3-thiocarboxylic acid-S-ethylester | 4 | 4 | 4 | 4 |
| 2-(dimethylcarbamoylimino)-benzothiazoline-3-carboxylic acid phenylester | 4 | 4 | 4 | 4 |

EXAMPLE 4

The plants listed below in Table 2 were treated in a hothouse in a preemergence application with the compounds listed also in the table. The compounds were employed in amounts of 1 kg of active agent per about 2.5 acres. The compounds for this purpose were applied in a uniform manner to the ground in the form of an aqueous suspension in 500 liters of water per about 2.5 acres.

The results show that the compounds of the invention have a high selectivity as distinguished from the comparison compound.

The tests are expressed on a scale from 0=total destruction of the plant, to 10=no damage to the plants.

for this purpose applied by uniform spraying onto the plants in the form of an aqueous suspension in 500 liters

TABLE II (Preemergence application)

| Compounds | kg active agent per 2.5 acres | sugar beets | peanuts | peas | maize | rice | seed-sorghum | potatoes | Stellaria m. | Senecio v. | Matricaria ch. | Lamium a. |
|---|---|---|---|---|---|---|---|---|---|---|---|---|
| 2-(dimethylcarbamoylimino)-benzothiazoline-3-carboxylic acid methylester | 1 | 10 | 10 | 10 | 9 | 8 | 10 | 10 | 0 | 0 | 0 | 0 |
| 2-(dimethylcarbamoylimino)-benzothiazoline-3-carboxylic acid butylester | 1 | 10 | 10 | 10 | 10 | 8 | 8 | 10 | 0 | 0 | 0 | 0 |
| 2-(dimethylcarbamoylimino)-benzothiazoline-3-carboxylic acid-(2-propenyl)-ester | 1 | 10 | 10 | 10 | 10 | — | — | 10 | 0 | 0 | 0 | 0 |
| 2-(dimethylcarbamoylimino)-benzothiazoline-3-carboxylic acid pentylester | 1 | 10 | 10 | 10 | 10 | 8 | 8 | 10 | 0 | 0 | 0 | 0 |
| 2-(dimethylcarbamoylimino)-benzothiazoline-3-carboxylic acid isobutylester | 1 | 8 | 10 | 10 | 10 | — | — | 10 | 0 | 0 | 0 | 0 |
| 2-(dimethylcarbamoylimino)-benzothiazoline-3-carboxylic acid isopropylester | 1 | 8 | 9 | — | 8 | — | — | 9 | 0 | 4 | 0 | 0 |
| 2-(dimethylcarbamoylimino)-benzothiazoline-3-carboxylic acid-(2-propinyl)-ester | 1 | 10 | 10 | 8 | 8 | 10 | 10 | 10 | 4 | — | 2 | 3 |
| 2-(dimethylcarbamoylimino)-benzothiazoline-3-carboxylic acid benzylester | 1 | 9 | 10 | 8 | — | 8 | 9 | 8 | 0 | 4 | 0 | 3 |
| 2-(dimethylcarbamoylimino)-benzothiazoline-3-thiocarboxylic acid-S-ethylester | 1 | 10 | 10 | 10 | 10 | 10 | 10 | 10 | 4 | — | — | — |
| Comparison compound 1-(benzothiazol-2-yl)-3,3-dimethyl urea | 1 | 9 | 8 | 2 | 9 | 8 | 4 | 9 | 0 | 0 | 0 | 0 |
| Untreated | — | 10 | 10 | 10 | 10 | 10 | 10 | 10 | 10 | 10 | 10 | 10 |

(Preemergence application)

| Compounds | Centaurea c. | Amaranthus r. | Chrysanthemum s. | Ipomea p. | Polygonum l. | Alopecurus m. | Digitaria s. | Poa a. |
|---|---|---|---|---|---|---|---|---|
| 2-(dimethylcarbamoylimino)-benzothiazoline-3-carboxylic acid methylester | 0 | 1 | 0 | 0 | 0 | 0 | 0 | 0 |
| 2-(dimethylcarbamoylimino)-benzothiazoline-3-carboxylic acid butylester | 0 | 0 | 0 | 0 | 0 | 2 | 1 | 0 |
| 2-(dimethylcarbamoylimino)-benzothiazoline-3-carboxylic acid-(2-propenyl)-ester | 0 | 0 | 0 | 0 | 0 | 1 | — | 0 |
| 2-(dimethylcarbamoylimino)-benzothiazoline-3-carboxylic acid pentylester | 0 | 0 | 0 | 0 | 0 | 2 | — | 0 |
| 2-(dimethylcarbamoylimino)-benzothiazoline-3-carboxylic acid isobutylester | 0 | 0 | 0 | 0 | 0 | 0 | 0 | 0 |
| 2-(dimethylcarbamoylimino)-benzothiazoline-3-carboxylic acid isopropylester | 0 | 0 | 0 | 0 | 0 | 2 | 4 | 0 |
| 2-(dimethylcarbamoylimino)-benzothiazoline-3-carboxylic acid(2-propinyl)-ester | — | — | 4 | — | — | — | — | 1 |
| 2-(dimethylcarbamoylimino)-benzothiazoline-3-carboxylic acid benzylester | 4 | 3 | 0 | — | 0 | 4 | 4 | 1 |
| 2-(dimethylcarbamoylimino)-benzothiazoline-3-thiocarboxylic acid-S-ethylester | — | — | — | — | — | — | — | — |
| Comparison compound 1-(benzothiazol-2-yl)-3,3-dimethyl urea | 0 | 0 | 0 | 0 | 0 | 0 | 0 | 0 |
| Untreated | 10 | 10 | 10 | 10 | 10 | 10 | 10 | 10 |

EXAMPLE 5

The plants listed in the Table 3 below were treated in a hothouse in a postemergence application with the agents also listed in the table in amounts of 1 kg of active agent per about 2.5 acres. The compositions were of water per about 2.5 acres.

Three weeks after treatment the results again showed that the compounds of the invention have a high selectivity combined with a superior activity against weeds. The comparison compound did not have a similar selectivity.

TABLE III

| (Postemergence application) Compounds | kg active agent per 2.5 acres | bush beans | pea- nuts | pota- toes | maize | wheat | barley | rice | seed- sorghum | Stell- caria m. | Senecio v. | Matri- aria ch. |
|---|---|---|---|---|---|---|---|---|---|---|---|---|
| 2-(dimethylcarbamoylimino) benzothiazoline-3-carboxylic acid methylester | 1 | — | 10 | 10 | 10 | 8 | 10 | 10 | 10 | 0 | 0 | 0 |
| 2-(dimethylcarbamoylimino)- benzothiazoline-3-carboxylic acid butylester | 1 | — | 9 | 10 | 10 | 10 | 10 | 10 | 10 | 0 | 0 | 0 |
| 2-(dimethylcarbamoylimino)- benzothiazoline-3-carboxylic acid-(2-propenyl)-ester | 1 | — | 10 | 10 | 10 | 10 | 10 | 10 | 10 | 0 | 3 | 0 |
| 2-(dimethylcarbamoylimino)- benzothiazoline-3-carboxylic acid pentylester | 1 | — | 10 | 10 | 10 | 10 | 10 | 10 | 10 | 0 | — | 0 |
| 2-(dimethylcarbamoylimino)- benzothiazoline-3-carboxylic acid isobutylester | 1 | — | 10 | 10 | 10 | 10 | 10 | 9 | 10 | 0 | 0 | 0 |
| 2-(dimethylcarbamoylimino)- benzothiazoline-3-carboxylic acid isopropylester | 1 | — | 8 | 10 | 10 | 9 | 10 | 10 | 10 | 0 | 0 | 0 |
| 2-(dimethylcarbamoylimino)- benzothiazoline-3-carboxylic acid-(2-propinyl)-ester | 1 | 8 | 9 | 10 | 10 | 8 | 8 | 10 | 10 | 0 | — | 0 |
| 2-(dimethylcarbamoylimino)- benzothiazoline-3-carboxylic acid benzylester | 1 | — | 8 | 9 | 8 | 8 | 8 | 10 | 10 | 1 | 4 | 0 |
| 2-(dimethylcarbamoylimino)- benzothiazoline-3-thiocar- boxylic acid-S-ethylester | 1 | — | 10 | 10 | 10 | 10 | 8 | 10 | 10 | 3 | — | 0 |
| Comparison compound | | | | | | | | | | | | |
| 1-(benzothiazol-2-yl)- 3,3-dimethyl urea | 1 | 1 | 5 | 1 | 5 | 4 | 5 | — | — | 0 | 0 | 0 |
| Untreated | — | 10 | 10 | 10 | 10 | 10 | 10 | 10 | 10 | 10 | 10 | 10 |

| (Postemergence application) Compounds | Lam- ium d. | Cen- tau- rea c. | Amaran- thus r. | Gali- um a. | Chry- san- the- mum s. | Ipo- mea p. | Poly- gonum l. | Alope- curus m. | Echin- och- loa c.g. | Seta- ria l. | Digit- aria s. | Poa a. |
|---|---|---|---|---|---|---|---|---|---|---|---|---|
| 2-(dimethylcarbamoylimino) benzothiazoline-3-carboxylic acid methylester | 0 | 0 | 0 | 0 | 0 | 0 | 0 | 2 | 0 | 0 | 0 | 0 |
| 2-(dimethylcarbamoylimino)- benzothiazoline-3-carboxylic acid butylester | 0 | 0 | 0 | 0 | 0 | 0 | 0 | 0 | 0 | 0 | 5 | 0 |
| 2-(dimethylcarbamoylimino)- benzothiazoline-3-carboxylic acid-(2-propenyl)-ester | 0 | 0 | 0 | 0 | 0 | 1 | 0 | — | — | 2 | 5 | 0 |
| 2-(dimethylcarbamoylimino)- benzothiazoline-3-carboxylic acid pentylester | 0 | 0 | 0 | 0 | 0 | 0 | 0 | — | — | 2 | 5 | 0 |
| 2-(dimethylcarbamoylimino)- benzothiazoline-3-carboxylic acid isobutylester | 0 | 0 | 0 | 0 | 0 | 2 | 0 | 5 | 1 | 0 | 5 | 0 |
| 2-(dimethylcarbamoylimino)- benzothiazoline-3-carboxylic acid isopropylester | 0 | 0 | 0 | 0 | 0 | 0 | 0 | 5 | 0 | 0 | 2 | 1 |
| 2-(dimethylcarbamoylimino)- benzothiazoline-3-carboxylic acid-(2-propinyl)-ester | 0 | 0 | 4 | 1 | 1 | 3 | 0 | — | — | 4 | — | — |
| 2-(dimethylcarbamoylimino)- benzothiazoline-3-carboxylic acid benzylester | 0 | 0 | 2 | 1 | 1 | 2 | 0 | 5 | — | 1 | — | 4 |
| 2-(dimethylcarbamoylimino)- benzothiazoline-3-thiocar- boxylic acid-S-ethylester | 2 | 2 | 4 | 4 | 0 | 3 | 1 | — | — | — | — | — |
| Comparison compound | | | | | | | | | | | | |
| 1-(benzothiazol-2-yl)- 3,3-dimethyl urea | 0 | 0 | 0 | 0 | 0 | 0 | 0 | 0 | 0 | 0 | 0 | 0 |
| Untreated | 10 | 10 | 10 | 10 | 10 | 10 | 10 | 10 | 10 | 10 | 10 | 10 |

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A compound of the formula

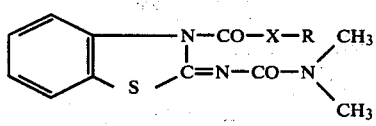

wherein

X is oxygen or sulfur; and

R is selected from the group consisting of $C_1$–$C_8$ alkyl, $C_2$–$C_8$ alkenyl, $C_2$–$C_8$ alkinyl, monohalobenzyl, dihalobenzyl and phenyl optionally mono-, di- or trisubstituted by one or more of halogen, $C_1$–$C_3$ alkyl, $C_1$–$C_3$ alkoxy, $C_1$–$C_3$ alkamino or trihalomethyl.

2. The carboxylic acid ester of claim 1 wherein R is methyl, ethyl, propyl, isopropyl, 2-propenyl, 2-propinyl, butyl, isobutyl, tert.-butyl, sec.-butyl, pentyl, isopentyl, hexyl, heptyl, octyl, phenyl, chlorophenyl, dichlorophenyl, benzyl, chlorobenzyl, dichlorobenzyl.

3. The compound of claim 1 which is 2-(dimethylcarbamoylimino)-benzothiazoline-3-carboxylic acid isopropylester.

4. The compound of claim 1 which is 2-(dimethylcarbamoylimino)-benzothiazoline-3-thiocarboxylic acid-S-ethylester.

5. The compound of claim 1 which is 2-(dimethylcarbamoylimino)-benzothiazoline-3-carboxylic acid methylester.

6. The compound of claim 1 which is 2-(dimethylcarbamoylimino)-benzothiazoline-3-carboxylic acid butylester.

7. The compound of claim 1 which is 2-(dimethylcarbamoylimino)-benzothiazoline-3-carboxylic acid-(2-propenyl)-ester.

8. The compound of claim 1 which is 2-(dimethylcarbamoylimino)-benzothiazoline-3-carboxylic acid pentylester.

9. The compound of claim 1 which is 2-(dimethylcarbamoylimino)-benzothiazoline-3-carboxylic acid isobutylester.

10. The compound of claim 1 which is 2-(dimethylcarbamoylimino)-benzothiazoline-3-carboxylic acid-(2-propinyl)-ester.

11. The compound of claim 1 which is 2-(dimethylcarbamoylimino)-benzothiazoline-3-carboxylic acid benzylester.

12. The compound of claim 1 which is 2-(dimethylcarbamoylimino)-benzothiazoline-3-carboxylic acid phenylester.

13. A herbicidal composition comprising at least one effective agent as defined in claim 1 in amounts between 10 and 80% by weight of total effective agents and about 90 to 20% by weight of a liquid or solid carrier material.

14. The composition of claim 13 which includes up to 20% of a surface active agent with a corresponding reduction in the other components.

* * * * *